Figure 1:
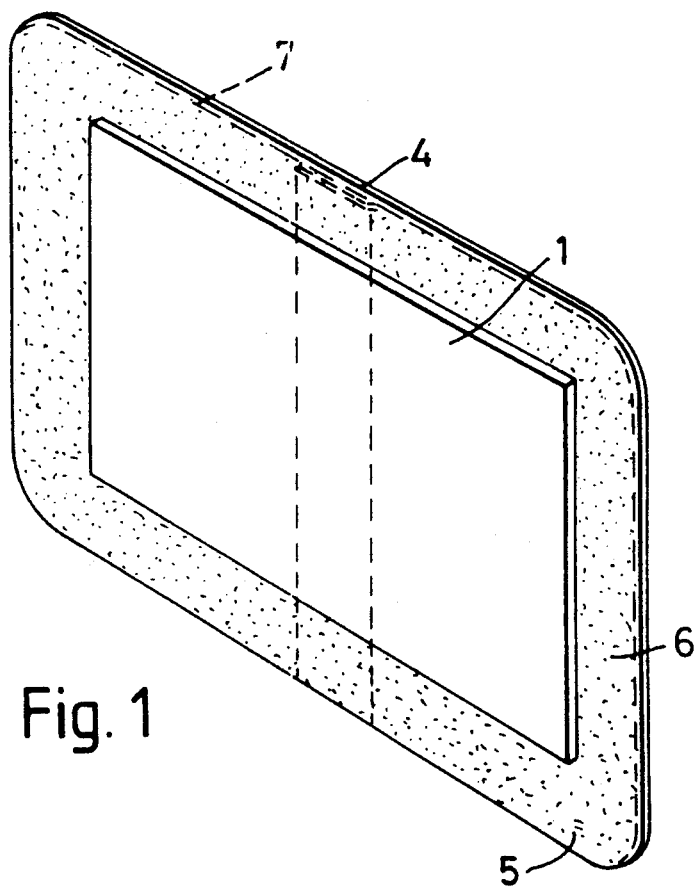

United States Patent [19]

Andrews

[11] Patent Number: 5,154,928
[45] Date of Patent: Oct. 13, 1992

[54] WOUND DRESSING

[75] Inventor: Trevor J. Andrews, Ashford, England

[73] Assignee: Uhra Laboratories Limited, United Kingdom

[21] Appl. No.: 529,876

[22] Filed: May 29, 1990

[51] Int. Cl.$^5$ .............................. A61L 15/00
[52] U.S. Cl. .................. 424/445; 424/400
[58] Field of Search ............ 424/445, 444, 443

[56] References Cited

U.S. PATENT DOCUMENTS

| | | | |
|---|---|---|---|
| 3,325,366 | 6/1967 | Blaug et al. | 424/444 |
| 4,730,611 | 3/1988 | Lamb | 424/445 |
| 4,746,514 | 5/1988 | Warne | 424/445 |
| 4,810,582 | 3/1989 | Gould et al. | 424/445 |
| 4,960,594 | 10/1990 | Honeycutt | 424/445 |

FOREIGN PATENT DOCUMENTS

| | | |
|---|---|---|
| 0164319 | 12/1985 | European Pat. Off. . |
| 0230387 | 7/1987 | European Pat. Off. . |
| 0235949 | 9/1987 | European Pat. Off. . |
| 0236104 | 9/1987 | European Pat. Off. . |

Primary Examiner—Thurman K. Page
Assistant Examiner—Leon R. Horne
Attorney, Agent, or Firm—Jones, Askew & Lunsford

[57] ABSTRACT

The invention provides a wound dressing comprising a pad of soft polyurethane foam one surface layer of which is hydrophilic and a backing layer of which is hydrophobic and a sheet or strip of a soft conformable polyether foam having an adhesive on one surface thereof. The surface of said pad opposite the hydrophobic layer is secured to said sheet or strip by said adhesive and said sheet or strip overlaps said pad to enable the pad to be secured in position with said hydrophilic layer in contact with a wound by means of said adhesive.

19 Claims, 1 Drawing Sheet

WOUND DRESSING

The present invention relates to wound dressings.

It is known from United Kingdom Patent Specifications Nos. 1417962 and 1450201 to provide a wound dressing comprising a pad of polyurethane material one surface layer of which has been modified to render it hydrophilic and the remainder of which is hydrophobic. Such wound dressings are used by placing the pad over the wound with the hydrophilic surface of the pad in contact with the wound and then securing the pad in place by adhesive strapping or by bandaging thereover. It is also known from U.S. Pat. No. 4,730,611 to provide a wound dressing comprising a foamed polyurethane as aforesaid positioned on a porous non-woven fibrous sheet of a larger selected size and having an adhesive on the side contacting the hydrophobic side of said pad so that the dressing presents the hydrophilic side and the adhesive for use in contact with a wound and the area surrounding the wound.

With wound dressings of the kind aforesaid it is desirable that the hydrophilic surface of the pad remain in close contact with the wound to remove exudates and to promote healing. With the known wound dressings this is difficult to achieve, particularly where the wound dressing is applied to an area subject to considerable movement such as an elbow joint or a knee joint, since conventional adhesive strapping and conventional bandaging either do not hold the pad in close contact with the wound over an extended period of time or can quickly work loose. The wound dressing comprising a polyurethane pad positioned on a porous non-woven fibrous sheet in accordance with the aforesaid United States patent has little elasticity and therefore does not readily conform for any extended period of time to difficult areas such as elbow joints and knee joints.

It is also desirable that a wound dressing should be impervious to water to enable a patient to bathe or shower without wetting or contaminating the wound but at the same time should be sufficiently porous to enable moisture to evaporate therethrough to maintain an environment under the dressing which will promote rapid healing of a wound. These requirements are not met by the known wound dressings.

The present invention therefore has as its object to provide a wound dressing which will overcome the limitations of the known wound dressings, which is highly conformable even to difficult areas of the body such as elbow joints or knee joints, which is water impermeable and which will allow moisture to evaporate therethrough.

The present invention provides a wound dressing comprising a pad of polyurethane foam one surface of which is hydrophilic and a backing layer of which is hydrophobic and a sheet or strip of a soft conformable polyether foam having an adhesive on one surface thereof, the surface of said pad opposite said hydrophilic layer being secured to said sheet or strip by said adhesive and said sheet or strip overlapping said pad to enable said pad to be secured in position with said hydrophilic layer in contact with a wound by means of said adhesive.

Said sheet or strip may overlap said pad on two opposite sides thereof although it is preferred that the sheet or strip overlap said pad around the whole of the periphery thereof.

A release paper or film may be applied over said adhesive, said release paper or film being removable prior to application of the wound dressing over a wound.

Said pad may have a thickness from 3 to 10 mm, preferably from 4 to 6 mm.

Said pad may be compressed around the periphery. Preferably, the compressed region extends inwardly for 5 mm to 10 mm from the edge, suitably 6 mm to 8 mm from the edge.

Preferably, the periphery is compressed to have a thickness of from 0.1 mm to 1.0 mm, suitably from 0.2 to 0.6 mm.

Said sheet or strip may be formed from a high density polyetherurethane foam, preferably a predominantly closed cell blocked toluene di-isocyanate polyetherurethane foam. Said polyetherurethane foam may have a pore size of 0.1 to 0.6 mm. The sheet or strip may have an elongation of 200% to 300%, preferably 240% to 270%. The sheet or strip may have a thickness of 0.2 to 1.0 mm, preferably 0.4 to 0.8 mm.

The said adhesive is preferably an acrylic adhesive but may be any of the other adhesives approved for medical use.

If desired, said pad may comprise at or adjacent said opposite surface thereof a layer impregnated with activated carbon for adsorbing organic odours. Thus, said impregnated layer may comprise a layer of non-woven viscose fibres on to which activated carbon granules have been sprayed. Said impregnated layer may be sandwiched between said sheet or strip and the hydrophobic backing layer of the pad or between two layers of hydrophobic polyurethane foam. Dressings comprising such an impregnated layer are useful when dressing wounds which give off an offensive odour as is the case, for example, with certain leg ulcers.

The wound dressing of the present invention may, in conventional manner, be sterile and be packaged in a sterile pack. For example said dressing and said pack may have been sterilised by gamma irradiation after packaging of the dressing in said pack.

Figure 2:
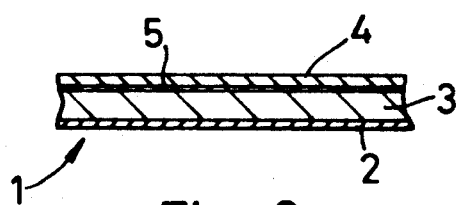
Figure 3:
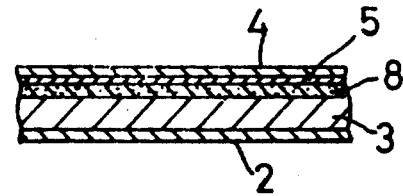
Figure 4:
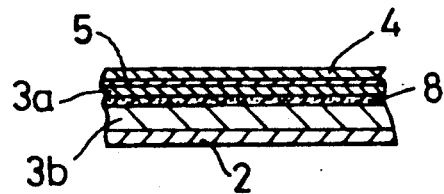
Figure 5:
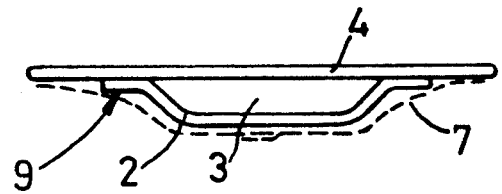

The invention will be more particularly described with reference to the accompanying drawings, in which FIG. 1 is an isometric view of a wound dressing according to the present invention, FIG. 2 is a fragmentary sectional elevation on an enlarged scale of the wound dressing of FIG. 1, FIG. 3 is a fragmentary sectional elevation on an enlarged scale of a modified wound dressing according to the present invention, FIG. 4 is a fragmentary sectional elevation of another modification of a wound dressing according to the invention, and FIG. 5 is a fragmentary sectional elevation of a further embodiment of a wound dressing according to the invention.

Referring to FIGS. 1 and 2 of the drawings it will be seen that the wound dressing illustrated therein comprises a pad 1 of soft polyurethane foam one surface layer 2 of which is hydrophilic and the remainder of which is hydrophobic and forms a backing layer 3 and a sheet or strip 4 of a soft conformable polyether foam having an adhesive 5 on one surface thereof, the surface of the hydrophobic layer 3 being secured to the sheet or strip 4 by said adhesive 5 and the sheet or strip 4 overlapping the pad 1 as shown at 6 to enable the pad 1 to be secured in position with the hydrophilic layer 2 in contact with a wound means of the adhesive 5. As will be seen from FIG. 1, the sheet or strip 4 overlaps the pad 1 around the whole of the periphery thereof. A release paper or release film 7, indicated by broken lines in FIG. 1, is applied over the adhesive 5 and over the pad 1 and is removable prior to application of the dressing over a wound.

The pad 1 has a thickness of from 3 to 10 mm, preferably 4 to 6 mm.

Referring to the embodiment shown in FIG. 5, the pad 1 is preferably compressed around its periphery. The compressed region 9 may extend inwardly for 5 mm to 10 mm from the edge, suitably 6 mm to 8 mm from the edge. Preferably, the periphery is compressed to have a thickness of from 0.1 to 1.0 mm, suitably from 0.2 to 0.6 mm.

Compressing the periphery of the pad 1 increases the effective border width without increasing overall dimensions or reducing the pad 1 area, to enable a more secure fixation of the wound dressing on the patient. Further, the release papers 7 thereby sits flat across the full width of the adhesive surfaces.

The compression of the periphery of the pad 1 is achieved prior to assembly of the wound dressing. The pad 1 is placed, with the hydrophilic surface layer 2 uppermost, centrally onto a forming tray with a cut out 14 mm smaller in all dimensions. The forming tray and wound dressing are then placed onto the lower, unheated, platen of a heat press. The lower platen is raised at a pressure in the range of 50 to 5000N/m$^2$, preferably 500 to 1500N/m$^2$, against the upper platen which is heated to a temperature of 140° C. to 250° C., preferably 180° C. to 200° C. After a period of time, preferably between 10 seconds and 90 seconds—suitably about 20 seconds—the pressure is released and the bottom platen lowered. The wound dressing so produced will have a periphery reduced in thickness.

The sheet or strip 4 in either embodiment is formed from a high density predominantly closed cell blocked toluene diisocyanate polyetherurethane foam. Preferably, the polyetherurethane foam from which the sheet or strip 4 is formed has a pore size of 0.1 to 0.6 mm and an elongation of 200% to 300%, preferably to 240% to 270%. The sheet or strip 4 may have a thickness of from 0.2 to 1.0 mm, preferably from 0.4 to 0.8 mm. The corners of the sheet or strip 4 are preferably rounded, to prevent them from lifting up when the wound dressing is in use.

The adhesive 5 is an acrylic adhesive although other adhesives approved for medical use may be used if desired.

The wound dressing illustrated in FIGS. 1 and 2 is highly conformable to different parts of the body, even to difficult parts such as elbow joints or knee joints, is waterproof so that a patient wearing the dressing can bathe or shower without danger of wetting or contaminating a wound and is sufficiently porous to enable moisture to evaporate therethrough.

As shown in FIGS. 3 and 4, in which like parts have been given like reference numerals, the pad 1 in either embodiment may include a layer 8 of non-woven fibres, e.g., viscose fibres, impregnated with granules of activated carbon. Thus, as shown in FIG. 3, the layer 8 may be provided between the hydrophobic layer 3 and the layer of adhesive 5 or, as shown in FIG. 4, the layer 8 may be sandwiched between hydrophobic layers 3a, 3b of the pad 1. A dressing incorporating the layer 8 is particularly useful for dressing wounds which give off an offensive odour, as is the case, for example, with certain leg ulcers and other wounds.

I claim:

1. A wound dressing comprising:
   a pad of soft polyurethane foam one surface layer of which is hydrophilic and a backing layer of which is hydrophobic;
   a sheet or strip of a soft conformable polyetherurethane foam having an adhesive on one surface thereof;
   the surface of said pad opposite said hydrophilic layer being secured to said sheet or strip by said adhesive; and
   the one surface of said sheet or strip overlapping said pad to enable said pad to be secured in position with said hydrophilic layer in contact with a wound by means of said adhesive.

2. A wound dressing according to claim 1, wherein said sheet or strip overlaps said pad on two opposite sides thereof.

3. A wound dressing according to claim 1, wherein said sheet or strip overlaps said pad around the whole of the periphery thereof.

4. A wound dressing according to claim 1 wherein a release paper or film is applied over said adhesive, said release paper or film being removable prior to application of the wound dressing over a wound.

5. A wound dressing according to claim 1 wherein said pad has a thickness of from 3 to 10 mm.

6. A wound dressing according to claim 1 wherein said pad has a thickness of from 4 to 6 mm.

7. A wound dressing according to claim 1 wherein said pad is compressed around the periphery.

8. A wound dressing according to claim 7, wherein the compressed region extends inwardly for 5 mm to 10 mm from the edge of the pad.

9. A wound dressing according to claim 7, wherein the periphery is compressed to have a thickness of from 0.1 mm to 1.0 mm.

10. A wound dressing according to claim 1 wherein said sheet or strip is formed from a high density polyetherurethane foam.

11. A wound dressing according to claim 10, wherein said sheet or strip is formed from a predominantly closed cell blocked toluene di-isocyanate polyetherurethane foam.

12. A wound dressing according to claim 10, wherein said polyetherurethane foam has a pore size of 0.1 to 0.6 mm.

13. A wound dressing according to claim 10, wherein said sheet or strip has an elongation of 200% to 300%.

14. A wound dressing according to claim 1, wherein said sheet or strip has a thickness of from 0.2 to 1.0 mm.

15. A wound dressing according to claim 1 wherein said adhesive is an acrylic adhesive.

16. A wound dressing according claim 1 wherein said pad comprises at or adjacent said opposite surface thereof a layer impregnated with activated carbon for adsorbing organic odours.

17. A wound dressing according to claim 16, wherein said impregnated layer comprises a layer of non-woven viscose fibres on to which activated carbon granules have been sprayed.

18. A wound dressing according to claim 16, wherein said impregnated layer is sandwiched between two layers of hydrophobic polyurethane foam.

19. A wound dressing comprising:

a pad of soft polyurethane foam one surface layer of which is hydrophilic and a backing layer of which is hydrophobic;

a sheet or strip of a soft conformable polyetherurethane foam having an adhesive on one surface thereof;

the polyetherurethane foam being a predominantly closed-cell blocked toluene diisocyanate polyetherurethane foam having a pore size of 0.1 to 0.6 mm and the sheet or strip having an elongation of 200% to 300%.

the surface of said pad opposite said hydrophilic layer being secured to said sheet or strip by said adhesive; and the one surface of said sheet or strip overlapping said pad to enable said pad to be secured in position with said hydrophilic layer in contact with a wound by means of said adhesive.

* * * * *